US 006750268B2

(12) United States Patent
Hino

(10) Patent No.: US 6,750,268 B2
(45) Date of Patent: *Jun. 15, 2004

(54) BONDING COMPOSITION

(75) Inventor: Kenichi Hino, Okayama-ken (JP)

(73) Assignee: Kuraray Co., Ltd., Kurashiki (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/994,613

(22) Filed: Nov. 28, 2001

(65) Prior Publication Data

US 2002/0061938 A1 May 23, 2002

Related U.S. Application Data

(62) Division of application No. 09/571,272, filed on May 15, 2000, now Pat. No. 6,387,979.

(30) Foreign Application Priority Data

May 13, 1999 (JP) ............................................ 11-132085

(51) Int. Cl.$^7$ .............................................. A61K 6/083
(52) U.S. Cl. ....................... 523/116; 523/117; 523/118; 522/908; 433/228.1
(58) Field of Search .................. 523/116–118; 522/908; 433/228.1

(56) References Cited

U.S. PATENT DOCUMENTS

| 4,668,712 A | | 5/1987 | Hino et al. .................... 522/13 |
| 4,719,149 A | | 1/1988 | Aasen et al. ................. 523/116 |
| 5,264,513 A | | 11/1993 | Ikemura et al. ............. 523/116 |
| 5,290,172 A | * | 3/1994 | Sakuma et al. ............. 433/215 |
| 5,321,053 A | | 6/1994 | Hino et al. |
| 5,525,648 A | | 6/1996 | Aasen et al. |
| 5,554,665 A | * | 9/1996 | Tateosian et al. ............. 522/30 |
| 5,859,089 A | * | 1/1999 | Qian .......................... 523/116 |
| 5,883,153 A | * | 3/1999 | Roberts et al. ............. 523/116 |
| 6,051,626 A | | 4/2000 | Zeng et al. |
| 6,147,137 A | * | 11/2000 | Jia ............................. 523/118 |
| 6,168,431 B1 | | 1/2001 | Narusawa et al. .......... 423/226 |
| 6,387,979 B1 | * | 5/2002 | Hino .......................... 523/116 |

* cited by examiner

*Primary Examiner*—Peter Szekely
(74) *Attorney, Agent, or Firm*—Oblon, Spivak, McClelland, Maier & Neustadt, P.C.

(57) ABSTRACT

A tooth treated with a bonding composition with high initial bonding strength and good bonding durability comprising a mixture of polymerizable compound having an acid group, a water-soluble film-forming agent, water, and a curing agent, in which the calcium salt of the acid is insoluble in water, and the film-forming agent is a polymerizable compound miscible with a physiological saline solution, does not require any pre-treatment such as acid-etching or priming treatment.

20 Claims, No Drawings

BONDING COMPOSITION

This application is a Division of application Ser. No. 09/571,272 filed on May 15, 2000, now U.S. Pat No. 6,387,979.

BACKGROUND OF THE INVENTION

1. Field of the Invention

The present invention relates to a self-etching and self-priming bonding composition for tooth restoration that keeps the restorative dental material bonded to the defective tooth for a long period of time.

2. Description of the Related Art

In the last half of the 20th century, the technology of bonding an acrylic resin to teeth had a great influence on the development of dental treatment. The first technique referred to is a technique developed by M. Buonocore in 1956. It comprises etching and roughening of the enamel of a tooth with an aqueous solution of phosphoric acid, resulting in a significant increase in the area of the bonding interface and an increase of the bonding strength between the tooth and the resin.

Later, various types of functional monomers capable of forming chemical bonds with the components of teeth have been developed. With those, the technique of bonding resins to the dentin of teeth has made remarkable progress in dental treatment. The proposed functional monomers include, for example, polymerizable monomers having an acid group, such as a phosphoric acid group or a carboxylic acid group, having high reactivity with the calcium hydroxyapatite (HAP) of teeth. Furthermore, other monomers capable of forming covalent bonds to the collagen of teeth have been proposed.

In Japanese Patent Laid-Open No. 45510/1985 the present applicant proposed a remarkable technique, wherein water is added to a dental bonding composition that contains a polymerizable monomer having a phosphoric acid residue. The dental bonding composition further comprises a specific terpolymerization initiator selected from diacyl peroxides, amine compounds, arylsulfinic acid salts, water, and optionally any other copolymerizable monomer. Conventionally it is assumed that the influence of water on the restored area of teeth is to be minimized to ensure good adhesion of a restorative material to teeth that are in constant contact with saliva. However, the disclosed invention is based on the finding that the bonding strength of the dental composition can be enhanced by adding water. The inventors disclose in the specification of 45510/1985 that the dental bonding composition exhibits high bonding strength even to the teeth not previously etched with an acid. The bonding strength may be further enhanced if the teeth are etched with an acid before the composition is applied. However, a self-etching or self-priming dental bonding composition is not disclosed.

After that, it was found that primers, if applied to teeth before the bonding composition, could enhance the bonding strength of the compositions to a great extent. Various proposals have been made for primers. Most of them ensured a complete wetting of the teeth by the bonding compositions. For example, Japanese Patent Laid-Open No. 223289/1987 discloses a primer for hard tissue which comprises an acid, a water-soluble film-forming agent, and optionally water. A specific acid is used in the invention. Its salt with calcium must be soluble in the water-soluble film-forming agent for the primer to provide high bonding strength. The specification discloses that the initial bonding strength of the bonding composition to the dentin of the tooth is increased if a primer is first applied to a tooth followed by the application of a bonding composition. However, when the bonded tooth sample is kept in water for a long period of time, the bonding strength of the bonding composition decreases, and the bonding durability is not satisfactory. Thus, the proposed primer has a drawback.

Japanese Patent Laid-Open No. 240712/1991 discloses a primer composition that comprises water, a polymerizable compound having a hydroxyl-group, a polymerizable compound having an acid group, and a curing agent. The object of the proposed primer is to provide high bonding strength and bonding durability. However, the polymerizable compound having an acid group is not specifically defined, and includes the polymerizable compounds that are exemplified as acids in the specification of above-mentioned 223289/1987.

The two techniques disclose a primer treatment of teeth instead of the ordinary etching with phosphoric acid to provide high bonding strength. However, bonding treatment with a liner or a similar bonding composition after the primer treatment is required when adhesive resin cement is used. Accordingly, the proposed techniques are still problematic because the use of primers does not shorten the process of dental treatment and does not fully meet the requirements of users and dentists.

The inventor has studied the mechanism of the bonding behavior and the bonding durability of the bonding compositions of above prior art. He found that the dentin of teeth is a complicated bio-tissue that comprises collagen fibers and HAP crystals. When an acidic primer having an acid ingredient is applied to dentin, it will partially dissolve the HAP crystals in the dentin. At the same time, the water-soluble monomer ingredient of the primer will penetrate into the collagen fibers remaining in the dentin after the HAP crystals were dissolved. As a result, the modified dentin surface is compatible with a bonding agent. The primer is then cured. The collagen fibers of the dentin will be entangled with the resin formed by polymerization of monomers and water-soluble film-forming agent. The bonding composition is applied to the tooth after the primer. As a result, the bonding composition has good bonding strength to the tooth.

The boundary area between the dentin of the tooth and the resin layer formed from the primer was analyzed. A calcium salt exists around the surface of the HAP crystals in the boundary area. The calcium salt was formed by reaction of above acid with HAP. In addition, resin portions containing the collagen fibers are left as they are after the partial dissolution of HAP. If the calcium salt of the acid is soluble in water it will gradually dissolve when the bonded sample is kept in water for a long period of time. Accordingly, the packing density of the bonding resin around the bonding interface will be lowered. As a result, the strength and durability of the bonding layer will also be lowered.

The present inventor has found the particular advantage of the prior art primers capable of exhibiting high bonding strength even when they are directly applied to teeth that are not previously subjected to acid etching (probably due to the self-etching effect of the primers). The present inventor further recognized the disadvantage of low bonding durability due to the solubility of the calcium salt of the acid in the bonding interface layer in water.

The present invention overcomes the drawback of the prior art primers on the basis of the fundamental knowledge relating to the composition of ordinary bonding compositions for dental use.

SUMMARY OF THE INVENTION

One object of the present invention is to provide a self-etching and self-priming bonding composition which ensures good initial bonding strength to teeth and long-lasting durability. The self-etching and self-priming bonding composition is useful in dental treatment and provides good bonding to tooth tissue and does not require any pre-treatment, such as acid etching and priming.

Another object of the invention is to provide a liquid bonding composition with rapid curability.

Still another object of the invention is to provide a bonding composition having the an increased bonding strength, whereby the thickness of the bonding layer can be controlled in any desired manner.

The objects of the invention are attained by providing a bonding composition which comprises:
- a mixture of a polymerizable compound having acid group, a water-soluble film-forming agent, water, and a curing agent;
- wherein a calcium salt formed from said polymerizable compound having an acid group is insoluble in water;
- wherein said film-forming agent is a polymerizable compound; and
- wherein said film-forming agent is miscible with a physiological saline solution.

DETAILED DESCRIPTION OF THE INVENTION

The inventor has found the following:

(1) Acids with a specific acid strength are preferred in bonding compositions for dental use. More preferred are those having a polymerizable group in the molecule that are capable of forming a stable chemical bond to HAP and the amino group of collagen of teeth as well as a stable chemical bond to a water-soluble polymerizable compound to be coated over teeth. Selective use of the specific acid in a bonding composition ensures better bonding durability.

(2) Preferred are those acids of which the calcium salts resulting from acid etching have a lower degree of solubility in water. If the calcium salt of the acid existing around the bonding interface does not dissolve in water, a lowering of the bonding strength of the resin may be prevented.

(3) Preferred are film-forming agents that are soluble in the acid to any desired degree and are copolymerizable with the acid. More preferred are those miscible with the fluid in body tissue, as they could well penetrate into hard tissue.

(4) Preferably, a polymerization initiator is added to bonding compositions. More preferably, polyfunctional monomers and others are added within a range not interfering with the uniformity of the compositions. They promote the polymerization of the bonding layer and make the polymerized bonding layer harder by introducing a cross-linked structure. The bonding strength and durability of the bonding layer are further enhanced.

(5) Preferably, a form-retaining agent is added to bonding compositions. It reinforces the bonding layer and, in addition, provides the desired thickness of the bonding layer. Accordingly, the polymerization inhibition in the bonding interface that may be caused by oxygen in air can be prevented. The bonding interface may be smoothly polymerized and cured for increased bonding strength of the cured bonding layer.

Based on his studies and the results as above, the inventor prepared samples of a bonding composition to be mentioned below, and tested them for their bonding behavior. The samples were applied to the dentin of bovine teeth and cured. Immediately after curing, the bonding layer had a bonding strength of at least 15 MPa. After the bonded samples were stored in water at 50° C. for one month, the bonding strength of the bonding layer was still at least 14 MPa. After the bonding test, the samples were observed, and most of them showed cohesive failure with the bonded tooth broken. The numerical data were obtained as above, but it is believed that the actual bonding strength of the bonding composition should be higher than the level of the data. On the basis of these findings, the inventor has reached and completed the present invention.

The polymerizable compound having an acid group may be soluble in water, or may dissolve in water to form micelles therein. Furthermore, the polymerizable compound may form an emulsion, a dispersion or a suspension. To provide good bonding of the composition, the polymerizable compound having an acid group is preferably as follows: When it is mixed with water to have a concentration of 1% by weight, the pH of the resulting mixture is at most 3, preferably at most 2.5 , more preferably falls between 1.8 and 2.5. The pH includes all values, therebetween, especially including a pH of 0.1, 0.5, 0.9, 1.2, 1.5, 1.8, 2.1, 2.4 and 2.7.

The calcium salt of the polymerizable compound having an acid group must be insoluble in water, and substantially insoluble in the film-forming agent. The solubility of the calcium salt of the acid may be determined as follows: A predetermined amount of calcium carbonate is added to a plurality of solutions having varying acid concentrations in water, or to a plurality of solutions having varying acid concentrations in a film-forming agent. 1.05 equivalent of acid is reacted with calcium carbonate to form a calcium salt. Where the reaction solution is clear the calcium salt has dissolved in the solution. However, where it is cloudy, the calcium salt did not dissolve. If the solubility of the calcium salt in water falls between 0.0001 and 0.05 mol/liter (M/L), then the calcium salt is insoluble in water, and satisfies the requirement of the invention. Preferably, the solubility of the calcium salt in water falls between 0.0001 and 0.01 MIL, more preferably between 0.0001 and 0.001 M/L.

The solubility includes all values therebetween, and especially including 0.0002, 0.0003, 0.0004, 0.0005, 0.0006, 0.0007, 0.0008, 0.0009, 0.001, 0.002, 0.003, 0.004, 0.005, 0.006, 0.007, 0.008 and 0.009 M/L.

Calcium salts of acids that are soluble in water to some degree just after their formation through reaction with teeth but are gradually converted into more stable insoluble salts are preferred compared to those that may be readily formed immediately after contact with teeth, such as salts of sulfuric acid. Preferably, the calcium salt of the acid is soluble to some degree in the acid-containing bonding composition. However, after the acid in the composition has completely reacted with a tooth, the resulting calcium salt is not soluble in the composition that does not contain any acid anymore. If hydrochloric acid, nitric acid, p-toluenesulfonic acid or the like are used in place of the polymerizable compound having an acid group, the solubility of the calcium salt of the acid in water is too high and the composition could not exhibit high bonding strength and durability. Therefore, these acids are unsuitable for the purpose of the present invention. On the other hand, the solubility of the calcium salts of phosphoric acid, oxalic acid or the like in water is too low, and the calcium salt of sulfuric acid crystallizes too rapidly. Therefore, the bonding composition containing any of these acids could not be self-etchable to a satisfactory degree, and the acids are not suitable for the present invention.

The polymerizable compound having an acid group is not specifically limited, as long as it satisfies the above solubility requirements. The following compounds are preferred for further improvement of the initial bonding strength and durability of the bonding composition: vinyl compounds having an acid group, such as a phosphoric acid group or a carboxyl group in the molecule. More preferred are vinyl compounds having a phosphoric acid group in the molecule. The vinyl compounds having a phosphoric acid group in the molecule include, for example, (meth)acryloyloxyalkyl phosphates (referring to acryloyloxyalkyl phosphates and methacryloyloxyalkyl phosphates), such as 2-(meth)acryloyloxyethyl phosphate, 2- or 3-(meth)acryloyloxypropyl phosphate, 4-(meth)acryloyloxbutyl 6-(meth)acryloyloxyhexyl phosphate, 8-(meth)acryloyloxyoctyl phosphate, 10-(meth)acryloyloxydecyl phosphate, 12-(meth)acryloyloxylauryl phosphate, 16-(meth)acryloyloxycetyl phosphate, 18-(meth)acryloyloxystearyl phosphate and 20-(meth)acryloyloxyeicosyl phosphate; di(meth)acryloyloxyalkyl phosphates such as 1,3-di(meth)acryloyloxypropyl-2 phosphate; (meth)acryloyloxyalkylaryl phosphates such as 2-(meth)acryloyloxyethylphenyl phosphate, 2-(meth)acryloyloxyethylphenyl phosphate and 2-(meth)acryloyloxyethyltolyl phosphate; (meth)acryloyloxyalkylaryl phosphonates such as 2-(meth)acryloyloxyethylphenyl phosphonate; (meth)acryloyloxyalkyl thiophosphates, such as 2-(meth)acryloyloxyethyl thiophosphate, 2- or 3-(meth)acryloyloxypropyl thiophosphate, 4-(meth)acryloyloxybutyl thiophosphate, 6-(meth)acryloyloxyhexyl thiophosphate, 8-(meth)acryloyloxyoctyl thiophosphate, 10-(meth)acryloyloxydecyl thiophosphate, 12-(meth)acryloyloxylauryl thiophosphate, 16-(meth)acryloyloxycetyl thiophosphate, 18-(meth)acryloyloxystearyl thiophosphate and 20-(meth)acryloyloxyeicosyl thiophosphate; di(meth)acryloyloxyalkyl thiophosphates such as 1,3 -di(meth)acryloyloxypropyl-2-thiophosphate; (meth)acryloyloxyalkylaryl thiophosphates such as 2-(meth)acryloyloxyethylphenyl thiophosphate, 2-(meth)acryloyloxyethylanisyl thiophosphate and 2-(meth)acryloyloxyethyltolyl thiophosphate; and (meth)acryloyloxyalkylaryl thiophosphonates such as 2-(meth)acryloyloxyethylphenyl thiophosphonate. Also employable are their precursors, which may be hydrolyzed in water to yield the acids. One or more of these may be used singly or in combination. They may be further combined with any other acid compound as long as the combinations attain the object of the invention. Preferred acid compounds are (meth)acryloyloxyalkyl phosphates in which the number of the carbon atoms constituting the alkyl group falls between 6 and 24, and more preferably between 8 and 20. Particularly preferred is 10-methacryloyloxydecyl phosphate (e.g., 10-methacryloyloxydecyl dihydrogenphosphate).

The vinyl compounds having a carboxyl group in the molecule include, for example, (meth)acryloyloxyalkoxycarbonylphthalic acids such as 4-(meth)acryloyloxyethoxycarbonylphthalic acid, 4-(meth)acryloyloxybutoxycarbonylphthalic acid, 4-(meth)acryloyloxyhexyloxycarbonylphthalic acid and 4-(meth)acryloyloxydecyloxycarbonylphthalic acid; (meth)acryloyloxyalkoxyalkoxycarbonylphthalic acids such as 4-(meth)acryloyloxyethoxyethoxycarbonylphthalic acid; dicarboxylic acids such as 11-(meth)acryloyloxyundecyl-1,1-dicarboxylic acid; and their anhydrides capable of being hydrolyzed to yield the acids. One or more of these may be used singly or in combination. They may be further combined with any other acid compound as long as the combinations attain the object of the invention. Preferred compounds are 4-(meth)acryloyloxyethoxycarbonylphthalic acid and 11 (meth)acryloyloxyundecyl-1,1-dicarboxylic acid.

The amount of the polymerizable compound having an acid group in the bonding composition of the invention may vary within a range provided the object of the invention is attained. Preferably, however, it falls between 0.1 and 50% by weight, more preferably between 1 and 50% by weight, even more preferably between 2 and 40% by weight of the bonding composition. These amounts include all values therebetween, and especially including 0.5, 1, 1.5, 2, 2.5, 3, 3.5, 4, 4.5, 5, 7.5, 10, 12.5, 15, 17.5, 20, 22.5, 25, 27.5, 30, 32.5, 35, 37.5, 40, 42.5, 45 and 47.5% by weight.

The film-forming agent differs from the polymerizable compound having an acid group mentioned above. It is a water-soluble polymerizable compound miscible with a physiological saline solution having a concentration of 9 g/L. Physiological saline solution may be a substituent for the fluid in body tissue. A mixture of two or more polymerizable compounds or a mixture of the film-forming agent with the polymerizable compound having an acid group and/or with an organic solvent can be used as the water-soluble film-forming agent. These mixtures can be soluble in water and miscible with a physiological saline solution even though they are not fully soluble in water and not miscible with a physiological saline solution by themselves. The bonding composition containing a film-forming agent of that type can form a uniform solution.

The film-forming agent must be soluble in water. Preferably, at least 5% by weight of the agent are soluble in water. More preferably, it is soluble in water in any ratio. In addition, the water-soluble film-forming agent must be miscible with a physiological saline solution. Whether the film-forming agent is miscible with a physiological saline solution or not can be determined from its phase diagram. For example, 50 parts by weight of the film-forming agent or the bonding composition is mixed with 50 parts by weight of a physiological saline solution at room temperature. The uniformity of the resulting solution is determined. Accordingly, the miscibility of the film-forming agent with a physiological saline solution can be determined in a simple manner.

The film-forming agent may be selected from acrylates, acrylamides, crotonates, cinnamates and others that are soluble in water and miscible with a physiological saline solution. However, preferred are (meth)acrylate monomers as they are easy to polymerize and safe to bodies. More preferred are (meth) acrylate monomers having an increased number of polar atoms, except carbon and hydrogen, in the molecule. Most preferably, the value obtained by dividing the total sum of the number of the polar atoms and the atomic weight of each polar atom, by the molecular weight of the (meth)acrylate molecule is at least 0.3.

Examples of (meth)acrylate compounds having a hydrophilic group such as a hydroxyl group, a carbonyl group, an amino group, an ammonium salt group, a phosphonium salt group, a sulfonic acid salt group, an ether bond, a cyclic ether group, an acyl group or the like in the molecule are given. They include, for example, hydroxyl group containing (meth)acrylates such as 2-hydroxyethyl (meth)acrylate, 2-hydroxypropyl (meth) acrylate, 1,3- and 2,3-dihydroxypropyl (meth)acrylates, pentaerythritol mono- and di(meth)acrylates, dipentaerythritol mono-, di- and tri(meth)

acrylates and xylitol mono- and di(meth)acrylates; amides such as (meth)acrylamide, 2-hydroxyethyl(meth) acrylamide, N,N-bis(2-hydroxyethyl)(meth)acrylamide, N-alkyl-N-hydroxyethyl(meth)acrylamides, 2- and 3-hydroxypropyl(meth)acrylamides and methacrylamidopropyltrimethylammonium chloride; glycol (meth) acrylates such as diethylene glycol mono(meth)acrylate, triethylene glycol mono(meth)acrylate, polyethylene glycol(400) mono(meth)acrylate and methoxypolyethylene glycol (meth)acrylate; other hydrophilic monomers such as dimethylaminoethyl (meth)acrylate, 2-trimethylammoniumethyl (meth)acrylate hydrochloride, pyrrolidone methacrylate and sorbitol (meth) acrylate. One or more of these may be used either singly or in combination. Preferred are hydroxyalkyl (meth)acrylates as hydrophilic monomers. Particularly preferred is 2-hydroxyethyl methacrylate. Preferably, it is the essential ingredient of the film-forming agent, for example, accounting for at least 50% by weight of the agent.

In case where two or more monomers are combined to give the film-forming agent, a plurality of the hydrophilic monomers as mentioned above can be selected and combined. If desired, any other monomers may be added thereto, as long as they satisfy the requirement that a mixture of 50 parts of the mixed film-forming agent and 50 parts of a physiological saline solution is a uniform solution. The additional monomers may be monofunctional (meth) acrylates, including, for example, methyl (meth)acrylate, ethyl (meth)acrylate, n-butyl (meth)acrylate, isobutyl (meth) acrylate, 2-ethylhexyl (meth)acrylate, lauryl (meth)acrylate, tridecyl (meth)acrylate, stearyl (meth)acrylate, cyclohexyl (meth)acrylate, benzyl (meth)acrylate, glycidyl (meth) acrylate, tetrahydrofurfuryl (meth)acrylate, allyl (meth) acrylate, methoxydiethylene glycol (meth)acrylate, methoxytetraethylene glycol (meth)acrylate, 2-ethoxyethyl (meth) acrylate, phenoxydiethylene glycol (meth)acrylate, phenoxyhexaethylene glycol (meth)acrylate, dicyclopentadiene-dimethanol-di(meth)acrylate, isobomyl (meth)acrylate, phenyl (meth)acrylate, caprolactone-modified tetrahydrofurfuryl (meth)acrylate, caprolactone-modified dipentaerythritol (meth)acrylate and caprolactone-modified 2-hydroxyethyl (meth)acrylate.

It is possible to use polyfunctional (meth)acrylates, including, for example, ethylene glycol di(meth)acrylate, diethylene glycol di(meth)acrylate, polyethylene glycol di(meth)acrylate, 2-hydroxypropyl-1,3-di(meth)acrylate, 1,3 -butylene glycol di(meth)acrylate, 1,6-hexanediol di(meth)acrylate, neopentylglycol di(meth)acrylate, tripropylene glycol di(meth)acrylate, polypropylene glycol di(meth)acrylate, bisphenol A di(meth)acrylate, bisphenol A-glycidyl di(meth)acrylate, ethylene oxide-modified bisphenol A di(meth)acrylate, ethylene oxide-modified bisphenol A-glycidyl di(meth)acrylate, 2,2-bis(4-methacryloxypropoxyphenyl)propane, 7,7,9-trimethyl-4, 13-dioxa-3,14-dioxo-5,12-diazahexadecane-1,16-diol di(meth)acrylate, neopentylglycol hydroxypivalate di(meth) acrylate, caprolactone-modified neopentylglycol hydroxypivalate di(meth)acrylate, trimethylolethane di(meth) acrylate, trimethylolpropane di(meth)acrylate, trimethylolmethane tri(meth)acrylate, trimethylolethane tri (meth)acrylate, trimethylolpropane tri(meth)acrylate, pentaerythritol tri(meth)acrylate, pentaerythritol tetra(meth) acrylate, dipentaerythritol tetra(meth)acrylate, dipentaerythritol hexa(meth)acrylate, reaction product of 3-chloro-2-hydroxypropyl (meth)acrylate and methylcyclohexane diisocyanate. reaction product of 2-hydroxypropyl (meth)acrylate and methylcyclohexane diisocyanate. reaction product of 2-hydroxypropyl (meth)acrylate and methylene bis(4-cyclohexyl isocyanate), reaction product of 2-hydroxypropyl (meth)acrylate and trimethylhexamethylene diisocyanate, reaction product of 2-hydroxyethyl (meth) acrylate and isophorone diisocyanate, reaction product of 3-chloro-2-hydroxypropyl (meth)acrylate and isophorone diisocyanate.

The film-forming agent may be a mixture that comprises, as the essential ingredient, any of the above-mentioned hydrophilic monomers and contains any of the above-mentioned monofunctional (meth)acrylates and/or polyfunctional (meth)acrylates. Preferably, the mixture contains a polyfunctional (meth)acrylate, to ensure better bonding durability of the bonding layer. In this case, the blend ratio of the monofunctional (meth)acrylate and/or the polyfunctional (meth)acrylate may fall between 0.1 and 40 parts by weight, preferably between 1 and 20 parts by weight to 100 parts by weight of the film-forming agent. The blend ratio includes all values therebetween, and especially including 0.2, 0.5, 1, 1.5, 2, 2.5, 5, 7.5, 10, 12.5, 15, 17.5, 20, 22.5, 25, 27.5, 30, 32.5, 35 and 37.5% per 100 parts by weight of the film-forming agent. The amount of the film-forming agent may vary within the range suitable for attaining the object of the invention. Preferably, it falls between 10 and 98% by weight, more preferably between 15 and 96% by weight, even more preferably between 20 and 90% by weight of the bonding composition. The amount of film-forming agent includes all values therebetween, especially including 15, 20, 25, 30, 35, 40, 45, 50, 55, 60, 65, 70, 75, 80, 85, 90, and 95% by weight of the bonding composition.

The bonding composition of the present invention must contain water to ensure the bonding ability. Preferably, water is in the products of the composition produced and distributed by manufacturers, but may be added thereto by dentists and other users after they have bought the products or just before they use them. Also preferably, the water is pure water such as distilled water, deionized water, water purified through reverse osmosis or the like. The used water may be tap water when the composition is used in field hospitals. It may be electrically pre-treated in an electric field. The amount of water may vary within the range suitable for attaining the object of the invention, but preferably falls between 1 and 80% by weight, more preferably between 10 and 70% by weight of the composition. The amount of water includes all values therebetween, especially including 2, 3, 4, 5, 7.5, 10, 12.5, 15, 17.5, 20, 22.5, 25, 27.5, 30, 32.5, 35, 40, 45, 50, 55, 60, 65, 70 and 75% by weight.

If desired, a water-soluble, volatile organic solvent may be added to the bonding composition of the present invention to augment the solvent effect of water in the composition. The organic solvent includes, for example, acetone, methyl ethyl ketone, methanol, ethanol and isopropyl alcohol. One or more of these organic solvents may be used either singly or in combination. Ethanol is particularly preferred. The amount of the organic solvent preferably falls between 1 and 50% by weight, more preferably between 2 and 40% by weight of the bonding composition. The amount of organic solvent includes all values therebetween, especially including 3, 5, 7, 9, 11, 13, 15, 17, 19, 21, 23, 25, 27, 29, 31, 33, 35, 37 and 39% by weight.

The bonding composition of the invention contains a curing agent. The curing agent may be a polymerization initiator generally used in ordinary bonding compositions, or may be a mixture of a polymerization initiator and a polymerization promoter. The polymerization initiator may be any of photo-polymerization initiators, thermal polymerization initiators and their mixtures. Preferably, it is soluble in water. However, if a polymerization initiator is poorly soluble in water, the bonding composition is preferably so conditioned that it does not deposit the initiator on the tooth tissue or does not precipitate the initiator while it is stored.

Preferred photopolymerization initiators are α-diketone compounds, ketal compounds. anthraquinone compounds, thioxanthone compounds. benzoin alkyl ether compounds and acylphosphine oxide compounds.

The α-diketone compounds include, for example, camphorquinone, benzil, diacetyl, acenaphthenequinone and 9,10-phenanthraquinone. The ketal compounds include, for example, benzyldimethyl ketal, benzyldiethyl ketal, benzyldi(β-phenylethyl) ketal and benzyldi(2-methoxyethyl) ketal. The anthraquinone compounds include, for example, anthraquinone, β-methylanthraquinone, and β-ethylanthraquinone. The thioxanthone compounds include, for example, 2-ethylthioxanthone, 2-chlorothioxanthone and 2-hydroxy-3-(3,4-dimethyl-9-oxo-9H-thioxanthen-2-yloxy)-N,N,N-trimethyl-1-propaneaminium chloride. The benzoin alkyl ether compounds include, for example, benzoin methyl ether, benzoin ethyl ether and benzoin propyl ether. The acylphosphine oxide compounds include, for example, 2,4,6-trimethylbenzoyldiphenylphosphine oxide, 2,6-dimethylbenzoyldiphenylphosphine oxide and 2,6-dimethoxybenzoyldiphenylphosphine oxide. Particularly preferred photopolymerization initiators are camphorquinone, benzil and 2,4,6-trimethylbenzoyldiphenylphosphine oxide.

Examples of thermal polymerization initiators are organic peroxides, including, for example, diacyl peroxides, peroxy esters, dialkyl peroxides, peroxy ketals, ketone peroxides and hydroperoxides. The diacyl peroxides include, for example, benzoyl peroxide, 2,4-dichlorobenzoyl peroxide and m-toluoyl peroxide. The peroxy esters includes, for example, t-butylperoxy benzoate, 2,5-dimethyl-2,5-bis (benzoylperoxy)hexane and t-butylperoxy-2-ethylhexanoate. The dialkyl peroxides include, for example, dicumyl peroxide, di-t-butylperoxide and lauroyl peroxide. The peroxy ketals include, for example, 1,1 -bis(t-butylperoxy)-3,3,5-trimethylcyclohexane. The ketone peroxides include, for example, methyl ethyl ketone peroxide. The hydroperoxides include, for example, cumemehydroperoxide and t-butylhydroperoxide. Particularly preferred is benzoyl peroxide as a thermal polymerization initiator.

Preferred polymerization promoters are amines, sulfinic acids and their salts. The amines are, for example, aromatic tertiary amines, and aliphatic tertiary amines. The aromatic tertiary amines include, for example, N,N-dimethylaniline, N,N-dimethyl-p-toluidine, N,N-diethyl-p-toluidine, N,N-dimethyl-3,5-dimethylaniline, N,N-dimethyl-4-ethylaniline, N,N-dimethyl-4-t-butylaniline, N,N-bis(2-hydroxyethyl)p-toluidine, N,N-bis(2-hydroxyethyl)-3,5-dimethylaniline, N,N-bis(2-hydroxyethyl)-3,4-dimethylaniline, N,N-bis(2-hydroxyethyl)-4-ethylaniline, N,N-bis(2-hydroxyethyl)-4-t-butylaniline, N,N-bis(2-hydroxyethyl)-3,5-di-t-butylaniline, ethyl 4-dimethylaminobenzoate, n-butoxyethyl 4-dimethylaminobenzoate, (2-methacryloyloxy)ethyl 4dimethylaminobenzoate and 4-dimethylaminobenzophenone. The aliphatic tertiary amines include, for example, trimethylamine, triethylamine, N-methyldiethanolamine, N-ethyldiethanolamine, N-n-butyldiethanolamine, N-lauryldiethanolamine, triethanolamine, (2-dimethylamino)ethyl methacrylate, N-methyldiethanolamine dimethacrylate, N-ethyldiethanolamine dimethacrylate, triethanolamine monomethacrylate, triethanolamine dimethacrylate, and triethanolamine trimethacrylate.

The sulfinic acids and their salts include, for example, benzenesulfinic acid, sodium benzenesulfinate, potassium benzenesulfinate, calcium benzenesulfinate, lithium benzenesulfinate, toluenesulfinic acid, sodium toluenesulfinate, potassium toluenesulfinate, calcium toluenesulfinate, lithium toluenesulfinate, 2,4,6-trimethylbenzenesulfinic acid, sodium 2,4,6-trimethylbenzenesulfinate, potassium 2,4,6-trimethylbenzenesulfinate, 2,4,6-triethylbenzenesulfinic acid, sodium 2,4,6-triethylbenzenesulfinate, potassium 2,4, 6-triethylbenzenesulfinate, 2,4,6-triisopropylbenzenesulfinic acid, sodium 2,4,6-triisopropylbenzenesulfinate and potassium 2,4,6-triisopropylbenzenesulfinate. Preferred are amines as polymerization promoters such as N,N-bis(2-hydroxyethyl)-p-toluidine, ethyl 4-dimethylaminobenzoate and n-butoxyethyl 4-dimethylaminobenzoate; and salts of sulfinic acids such as sodium benzenesulfinate, sodium toluenesulfinate and sodium 2,4,6-triisopropylbenzenesulfinate.

The amount of the curing agent may vary within the range suitable for attaining the object of the invention. It may fall generally between 0.05 and 20% by weight, but preferably between 0.1 and 20% by weight, more preferably between 1 and 10% by weight of the bonding composition. The amount of the curing agent includes all values therebetween, especially including 0.15, 0.25, 0.35, 0.45, 0.5, 1, 2, 3, 4, 5, 6, 7, 8, 9, 10, 11, 12, 13, 14, 15, 16, 17, 18 and 19% by weight.

The method of adding the curing agent to the bonding composition of the invention is not specifically limited, as long as it attains the object of the invention. For example, in case where the bonding composition is to be cured by photopolymerization, it may be packed a single package containing both a photopolymerization initiator and a polymerization promoter. However, if it contains a thermal polymerization initiator and a polymerization promoter, it may be divided into two or more packages so that a peroxide and an amine or a peroxide and a salt of a sulfinic acid are not in one and the same package, in order to ensure the storage stability of the composition. Two or more packages separately containing the constituent ingredients of the bonding composition may be blended before use. If the bonding composition is applied twice or more to a surface, another method may be employed. For example, one part of the composition containing a polymerization initiator is first applied to an object, and thereafter another part containing a polymerization promoter alone is applied thereto. This is for ensuring the migration and mixture of the ingredients of the curing agent on the surface of the object. The blend ratio of all the ingredients constituting the bonding composition applied to the object must satisfy the requirement of the invention.

As so mentioned hereinabove, the bonding composition of the invention contains a curing agent, and the curing agent may be a polymerization initiator alone, or a mixture of a polymerization initiator and a polymerization promoter. Preferably, the bonding composition is curable as rapidly as possible, since the thickness of the uncured surface layer of the composition applied to an object can be thinner. If the rapidly-curable composition is applied to an object to a predetermined level, its cured layer has the intended thickness, and the bonding interface is protected from oxygen that may act as a polymerization inhibitor. As a result, the bonding interface can be highly polymerized. Accordingly, the polymerization initiator enables easy and rapid polymerization of the bonding composition and ensures the storage stability thereof. The photopolymerization initiator gets energy, after having absorbed light forming active radicals. It is generally combined with a polymerization promoter that promotes the radical formation. Such photopolymerization initiator may be additionally combined with a thermal polymerization initiator, and the combination is effective in the invention. Preferably, the bonding composition of the invention is a photopolymerizable liquid bonding composition in the form of one single package containing all the necessary constituent ingredients therein. Though not intended, however, the active ingredients of the composition in such single packages may degrade or polymerize while stored. To prevent this, the constituent ingredients of the composition may be divided into two or more parts. The plural parts are separately packaged and stored in different packages. For their use, the plural parts taken out of the individual packages may be applied to one and the same object in sequence; or they may be blended into one mixture just before use.

Further preferably, the bonding composition of the present invention contains a form-retaining agent. The form-retaining layer acts to control the thickness of the bonding layer of the composition. Specifically, it reinforces the bonding layer and ensures the desired thickness of the bonding layer. Accordingly, inhibition of the polymerization in the bonding interface caused by oxygen in air can be prevented, and the bonding interface can be smoothly polymerized and cured to provide increased bonding strength. In general, the thickness of the bonding layer is controlled to fall between 20 and 300 micron, preferably between 20 and 100 micron. The thickness of the bonding layer includes all values therebetween, especially including 40, 60, 80, 100, 120, 140, 160, 180, 200, 220, 240, 260 and 280 micron.

For its morphology, the form-retaining agent is not specifically limited, and may be any of granular, tabular, sheet-like, fibrous or porous structure. In view of its handle ability, the form-retaining agent is preferably granular. Furthermore, a hydrophobic polymerizable composition, for example, a dental restorative composite resin is applied to the site to which the bonding composition is applied. Therefore, it is desirable that the form-retaining agent is treated, for example, with a silane coupling agent to improve its compatibility with composite resins. It is desirable that the particles of the form-retaining agent are not too fine to prevent an increase of the viscosity of the bonding composition. It is preferred that the particles of the form-retaining agent are large enough to allow for free movement of a liquid component along with them. However, they do not almost move by themselves to increase the viscosity of the bonding composition. For example, the form-retaining agent may have a mean particle size of from 1 to 300 micron, preferably from 3 to 100 microns, more preferably from 5 to 80 micron. The mean particle size includes all values therebetween, especially including 2, 3, 4, 6, 7, 8, 9, 10, 20, 40, 60, 80, 100, 120, 140, 160, 180, 200, 220, 240, 260 and 280 micron.

The form-retaining agent includes, for example, sand balloons, glass balloons, short glass fibers, pieces of hollow glass fibers, glass beads, glass powders, powders of various natural minerals, beads and flakes of various crosslinked polymers, organic/inorganic composite materials containing such inorganic substances and crosslinked polymers. Preferred form-retaining agents are crosslinked polymers because they do not solidify through precipitation or aggregation in the bonding composition and their specific gravity can be nearly the same as that of the bonding composition. The granular crosslinked polymers may be prepared, for example, through suspension or emulsion copolymerization of the above-mentioned monofunctional (meth)acrylates and polyfunctional (meth)acrylates. The crosslinked polymers may be swollen when mixed with the bonding composition comprising a polymerizable compound containing an acid group, a film-forming agent and an organic solvent. In general, the degree of swelling of the crosslinked polymers in those ingredients may be at most 100%.

The amount of the form-retaining agent that may be in the bonding composition of the present invention may fall between 0.5 and 20% by weight, preferably between 1 and 10% by weight. The amount of form-retaining agent includes all values therebetween, especially including 1.5, 2.5, 5, 7.5, 10, 12.5, 15 and 17.5% by weight.

The method to be employed herein for preventing the form-retaining agent from aggregating and solidifying in containers is not specifically limited. For example, hard balls, cylindrical or oval blocks may be put in the container with the bonding composition. The container is shaken to agitate the contents before the composition is used. In this method, the specific gravity of the form-retaining agent can be neglected without problem.

As mentioned above, the bonding composition preferably comprises from 1 to 50% by weight of a polymerizable compound having an acid group, from 10 to 96% by weight of a water-soluble film-forming agent, from 1 to 80% by weight of water, and from 0.1 to 20% by weight of a curing agent. More preferably the bonding composition comprises from 1 to 50% by weight of a polymerizable compound having an acid group from 10 to 96% by weight of a water-soluble film-forming agent, from 1 to 80% by weight of water, from 0.1 to 20% by weight of a curing agent, and from 0.5 to 20% by weight of a form-retaining agent. If desired, additives generally used in ordinary bonding compositions, for example, pigments or dyes for differentiation, viscosity improvers for attaining optimum viscosity and others may be added to the bonding composition of the invention, as long as they do not have any negative influences on the composition.

Having generally described this invention, a further understanding can be obtained by reference to certain specific examples which are provided herein for purposes of illustration only, and are not intended to be limiting unless otherwise specified.

EXAMPLES

Measurement of pH

One part by weight of the acid to be measured is mixed with 99 parts by weight of distilled water, and the pH of the resulting mixture is measured with a pH meter (Iuchi's pH meter).

Measurement of Solubility of a Calcium Salt of an Acid in Water

The acid to be measured (0.21 mmols for monoacid, 0.105 mmols for diacid) and distilled water (1 ml) are put into a 20 ml test tube, and stirred therein for 10 minutes so that the acid is dissolved in the water. Next, powdery calcium carbonate (0.1 mmols) is fed into the test tube, and stirred at room temperature for 10 minutes so that it is reacted with the acid. The resulting solution is macroscopically checked as to whether it is clear or cloudy. The solubility of the calcium salt in the clear solution is above 0.1 M/L, and the acid is marked "x".

To the cloudy solution in the test tube, 9 ml of distilled water is further added, and stirred at room temperature for 30 minutes. This is again checked macroscopically. When it gives a clear solution in this condition, the solubility of the calcium salt falls between 0.01 and 0.1 M/L, and the acid is marked "Δ". When it is still cloudy in this condition, the solubility of the calcium salt is below 0.01 M/L, and the acid is marked "O". In case where the solubility of the calcium salt of the acid tested is numerically represented, test tubes having a proper capacity are prepared, and the process as above is repeated in them. Salt solutions having different concentrations are prepared, and they are macroscopically checked to quantitatively determine the solubility of the salt.

Measurement of Solubility of Calcium Salt of Acid in Film-forming Agent

The acid to be measured (0.21 mmols for monoacid, 0.105 mmols for diacid) and distilled water (1 ml) are put into a 20 ml test tube, and stirred therein for 10 minutes so that the acid is dissolved in the water. Next, powdery calcium carbonate (0.1 mmols) is fed into the test tube, and stirred at room temperature for 10 minutes so that it is reacted with the acid to give a calcium salt of the acid. Next, the resulting solution is dried in a drier at 60° C. for 16 hours to remove water, and the 1 ml of a film-forming agent is added to the resulting residue. This is stirred at room temperature for 30 minutes, and the resulting solution is macroscopically checked as to whether it is clear or cloudy. The solubility of the calcium salt in the clear solution is above 0.1 M/L, and the acid is marked "x".

To the cloudy solution in the test tube, 9 ml of the film-forming agent is further added, and stirred at room temperature for 30 minutes. This is again checked macroscopically. When it gives a clear solution in this condition, the solubility of the calcium salt falls between 0.01 and 0.1 M/L, and the acid is marked "Δ". When it is still cloudy in this condition, the solubility of the calcium salt is below 0.01 M/L, and the acid is marked "O". For easily-available calcium salts of acids, such as calcium chloride. calcium nitrate and others, they are not produced in the manner as above, but commercial products are used to measure their solubility.

Measurement of Bonding Strength to the Enamel or the Dentin of Bovine Teeth

A bovine, mandibular incisor (this is as large as possible) is used as the object to which the bonding composition to be tested is bonded. Its center that faces the lips is abraded first with waterproof abrasive paper, #320 and finally with #1000 to make a flat surface in enamel portion or in dentin portion. On the flat surface thus-exposed in enamel or dentin, a mending tape (from 3M) with a circular hole (diameter: 3 mm) is stuck in its center, by which the area of the enamel or the dentin to which the bonding composition is applied is defined. 14 bovine tooth samples are prepared for every bonding composition to be tested herein.

The bonding test is effected as follows: In a place where a gentle stream is running (around the inlet of a draft chamber), the bonding composition to be tested is fully applied onto the surface of the exposed enamel or dentin of the bovine tooth sample (its layer formed is about 500 microns thick), and processed as such for 60 seconds. Next, this is exposed to mild air blow so that water and other volatile components are removed to such a degree that the surface of the bonding composition on the dentin is kept glossy. Next, this is exposed to visible rays from a dental light emitter (Ushio Electric's Litel 2) for 20 seconds, and a photopolymerizable dental composite resin, Clearfill Photo SC (from Kuraray, this is for restoring carious teeth) is applied thereover to form a layer of a few mm thick thereon. Then, this is gently pressed against a glass slide superimposed thereon. In that condition, this is again exposed to light from the same light emitter as above for 20 seconds so that the composite resin is cured. One end of a stainless steel rod of SUS-304 having a diameter of 5 mm (the other end thereof is holed so that a pin could be fitted therein, and a jig to measure the tensile strength of the bonded sample is fitted to the pin) is attached to the bonded sample vertically to the enamel or dentin surface of the sample, via a dental resin cement (Kuraray's Panavia 21) therebetween. In that condition, the sample is stored in water at 37° C. for 2 hours. Thus prepared, seven of 14 samples in one group are subjected to a tensile test, for which is used an Instron universal tester. The cross head speed in the test is 2 mm/min. Five of seven data obtained, excepting the highest and lowest data, are averaged, and the averaged value indicates the bond strength of the samples of the group.

Measurement of Bonding Durability

The remaining seven samples prepared above, which are still in water, are stored as such in a thermostat water tank at 50° C. for one month. The thus-stored samples are subjected to the same tensile test as above to measure their bond strength. The data obtained indicate the bonding durability of the samples.

The meanings of the abbreviations used herein are mentioned below.

HEMA: hydroxyethyl methacrylate
HPMA: hydroxypropyl methacrylate
GLM: glycerol monomethacrylate
PE-200-OH: monomethacrylate of polyethylene glycol 200
PE-200-OMe: methacrylate of methoxypolyethylene glycol 200
PE-200-OMR: dimethacrylate of polyethylene glycol 200
HO-4ED: monomethacrylate of ethylene glycol tetra- or penta-mer
3G: dimethacrylate of ethylene glycol trimer
9G: dimethacrylate of ethylene glycol nona-mer
14G: dimethacrylate of ethylene glycol tetradeca-mer
BMHPE: 1,2-bis(3-methacryloxy-2-hydroxypropoxy)ethane
PMEP: phenyl-2-methacryloyloxyethyl phosphate
2MEP: 2-methacryloyloxyethyl phosphate
8MOP: 8-methacryloyloxyoctyl phosphate
9MNP: 9-methacryloyloxynonyl phosphate
10MDP: 10-methacryloyloxydecyl phosphate
12MLP: 12-methacryloyloxydodecyl phosphate
MRA: methacrylic acid
TSA: p-toluenesulfonic acid
Bis-GMA: 2,2-bis[4-(3-methacryloyloxy-2-hydroxypropoxy)phenyl]propane
MMA: methyl methacrylate
TMTA: trimethylolpropane triacrylate
UDMA: [2,2(4),4-trimethylhexamethylenebis(2-carbamoyloxyethyl)] dimethacrylate Reference Example (Solubility of Film-forming Agent)

About 1 g of the film-forming agent shown in Table 1 below was metered into a 5 ml glass bottle, and a physiological saline solution with a concentration of 9 g/L of which the weight was the same as that of the film-forming agent was put into the glass bottle, and shaken at room temperature for 20 seconds. The resulting mixture was macroscopically checked as to whether or not it could be a uniform solution. The results obtained are given in Table 1.

TABLE 1

Uniformity of Reference Solutions

| Film-forming Agent | Solubility | Film-forming Agent | Blend Ratio (wt. %) | Solubility |
|---|---|---|---|---|
| HEMA | dissolved | HEMA/BMHPE | 50/50 | not dissolved |
| HPMA | not dissolved | HEMA/BMHPE | 60/40 | dissolved |
| GLM | dissolved | HEMA/BMHPE | 70/30 | dissolved |
| PE-200-OH | dissolved | HEMA/3G | 90/10 | dissolved |
| PE-200-OMe | not dissolved | HEMA/9G | 23/77 | dissolved |
| PE-200-OMR | not dissolved | HEMA/9G | 50/50 | dissolved |
| HO-4ED | dissolved | GLM/9G | 23/77 | dissolved |
| 9G | no dissolved | GLM/9G | 50/50 | dissolved |
| 14G | dissolved | | | |
| BMHPE | not dissolved | | | |

Examples 1 to 6, Comparative Examples 1 to 8

Acids shown in Table 2 below were used. Bonding compositions comprising 10 parts by weight of the acid, 50 parts by weight of a film-forming agent composed of 90% by weight of HEMA and 10% by weight of BMHPE, 40 parts by weight of distilled water, 0.5 parts by weight of camphorquinone, 0.5 parts by weight of N,N-dimethylaminobenzophenone, and 0.5 parts by weight of 2,4,6-trimethylbenzoyldiphenylphosphine oxide were prepared, and their bonding strength and bonding durability were measured according to the methods mentioned above. The data obtained are given in Table 2. In the bond strength test, the bonded samples of Comparative Examples 1 to 8 peeled at the interface between the bovine tooth and the bonding layer; but in the bonded samples of Examples 1 to 6, several bovine tooth were broken. In particular, almost all the bonded samples of Examples 3 to 6 showed cohesive failure with the bonded bovine tooth broken.

From the results obtained, it is understood that the bonding compositions containing a polymerizable compound having an acid group, of which the solubility of the calcium salt in water and in the film-forming agent in the composition is smaller than 0.01 M/L (this means the calcium salt is insoluble in both), all have extremely high bonding strength and extremely good bonding durability.

Examples 7 to 10

Acids shown in Table 3 below were used. Bonding compositions comprising 5 parts by weight of the acid, 30 parts by weight of a film-forming agent composed of 65% by weight of HEMA and 30% by weight of BMHPE and 5% by weight of Bis-GMA, 30 parts by weight of distilled water, 35 parts by weight of ethanol, 0.3 parts by weight of camphorquinone, 0.3 parts by weight of N,N-dimethylaminobenzophenone, 0.3 parts by weight of 2,4,6-trimethylbenzoyldiphenylphosphine oxide, and 2 parts by weight of particles of fused quartz glass (these were prepared by grinding a solid of fused quartz glass into particles of not larger than 25 microns in size, removing fine powder from them through precipitation, and treated them with silane coupling agent, and had a mean particle size of 10 microns) were prepared. Just before use, these were well shaken, and their bonding strength and bonding durability were measured according to the methods mentioned above. The data obtained are given in Table 3. The bonding strength and the bonding durability of all the bonded samples were at least 16 MPa. Almost all of them showed cohesive failure with the bonded bovine tooth broken. From the results obtained, it is understood that the bonding compositions additionally containing a form-retaining agent have more increased bonding strength and more stable bonding durability.

TABLE 2

| | Type of Acid | pH of Acid | Calcium Salt of Acid Solubility in water | Calcium Salt of Acid Solubility in Film-forming Agent | Bonding Strength (MPa) | Bonding Durability (MPa) |
|---|---|---|---|---|---|---|
| Example 1 | PMEP | 1.7 | ○ | ○ | 15.3 | 12.9 |
| Example 2 | 2MEP | 1.7 | ○ | ○ | 15.1 | 9.4 |
| Example 3 | 8MOP | 2.2 | ○ | ○ | 18.2 | 14.0 |
| Example 4 | 9MNP | 2.2 | ○ | ○ | 17.9 | 14.2 |
| Example 5 | 10MDP | 2.3 | ○ | ○ | 18.6 | 15.8 |
| Example 6 | 12MLP | 2.3 | ○ | ○ | 18.0 | 15.5 |
| Comp. Ex. 1 | MRA | 2.9 | X | ○ | 9.8 | 4.4 |
| Comp. Ex. 2 | hydrochloric acid | 0.9 | X | ○ | 10.2 | 5.0 |
| Comp. Ex. 3 | nitric acid | 0.9 | X | ○ | 12.5 | 6.2 |
| Comp. Ex. 4 | TSA | 1.4 | X | ○ | 12.7 | 7.0 |
| Comp. Ex. 5 | phosphoric acid | 1.6 | ○ | ○ | 5.5 | — |
| Comp. Ex. 6 | oxalic acid | 1.3 | ○ | ○ | 4.2 | — |
| Comp. Ex. 7 | sulfuric acid | 1.1 | X | ○ | 3.7 | — |
| Comp. Ex. 8 | citric acid | 1.6 | X | ○ | 4.7 | — |

TABLE 3

| | Type of Acid | pH of Acid | Calcium Salt of Acid Solubility in Water | Calcium Salt of Acid Solubility in Film-forming Agent | Bonding Strength (MPa) | Bonding Durability (MPa) |
|---|---|---|---|---|---|---|
| Example 7 | 8MOP | 2.2 | ○ | ○ | 19.3 | 16.0 |
| Example 8 | 9MNP | 2.2 | ○ | ○ | 18.5 | 16.1 |

TABLE 3-continued

|  | Type of Acid | pH of Acid | Calcium Salt of Acid Solubility in Water | Solubility in Film-forming Agent | Bonding Strength (MPa) | Bonding Durability (MPa) |
| --- | --- | --- | --- | --- | --- | --- |
| Example 9 | 10MDP | 2.3 | ○ | ○ | 18.6 | 17.6 |
| Example 10 | 12MLP | 2.3 | ○ | ○ | 19.0 | 18.5 |

Examples 11 to 15

A mixture comprising 10 parts by weight of 10-methacryloyloxydecyl phosphate (the solubility in water of its calcium salt was 0.0003 M/L and the solubility thereof in the film-forming agent used herein was 0.0001 M/L, the latter being obtained through emission spectrometry using a light source of ICP), 30 parts by weight of a film-forming agent composed of 65% by weight of HEMA, 30% by weight of BMHPE and 5% by weight of Bis-GMA, 30 parts by weight of distilled water, 0.3 parts by weight of camphorquinone, 0.3 parts by weight of (2-methacryloyloxy)ethyl N,N-dimethylaminobenzoate, and 30 parts by weight of ethanol was mixed with 5 parts by weight of the form-retaining agent shown in Table 4 to prepare bonding compositions. Just before use, these were well shaken, and their bonding strength and bonding durability were measured according to the methods mentioned above. The data obtained are given in Table 4. From the results obtained, it is understood that the bonding compositions of these Examples all have extremely high bonding strength and extremely good bonding durability, like those of Examples 7 to 10.

TABLE 4

|  | Form-retaining Agent | | Bonding Strength (MPa) | Bonding Durability (MPa) |
| --- | --- | --- | --- | --- |
|  | particle size (μm) | Material |  |  |
| Example 11 | 35 | hollow borosilicate glass 1) | 20.7 | 18.6 |
| Example 12 | 50 | alumina for sand blasting 2) | 21.2 | 18.1 |
| Example 13 | 60 | plastic beads 3) | 17.5 | 17.1 |
| Example 14 | 15 | organic composite filler 4) | 17.1 | 16.0 |
| Example 15 |  | glass cloth 5) | 18.8 | 18.0 |

1) Fuji Silicia's glass balloon S-35
2) Jelenco's product
3) Negami Kogyo's TM-150 (MMA/TMTA)
4) Kuraray's UDMA/3G/Aerosil OX-50-30/10/60
5) A knitted sheet of glass fibers having a fiber diameter of 10 μm was cut to give a disc having a diameter of 3 mm.

Example 16

To 97 g of a mixture comprising 5 parts by weight of 4-methacryloyloxyethoxycarbonylphthalic acid, 45 parts by weight of HEMA, 10 parts by weight of BMHPE, 20 parts by weight of distilled water, 20 parts by weight of ethanol, 0.5 parts by weight of camphorquinone, and 0.3 parts by weight of ethyl N,N-dimethylaminobenzoate, added was 3 g of silane-treated, hollow borosilicate glass of 35 microns in size, and well mixed to prepare a bonding composition. Its bonding strength and bonding durability were measured according to the methods mentioned above, and were 16.7 MPa and 15.0 MPa, respectively.

Comparative Examples 9 to 12

Bonding compositions were prepared in the same manner as in Example 5, except that the acid only was omitted (Comparative Example 9), the film-forming agent only was omitted (Comparative Example 10), water only was omitted (Comparative Example 11), and the curing agent only was omitted (Comparative Example 12). Their bonding strength and bonding durability were measured according to the same methods as in Example 5. The data obtained are given in Table 5. From these, it is understood that the composition not containing the acid is not adhesive and that the compositions not containing any of the film-forming agent, water and the curing agent have poor bonding strength and poor bonding durability.

TABLE 5

|  | Bonding Strength (MPa) | Bonding Durability (MPa) |
| --- | --- | --- |
| Comparative Example 9 | 0 | 0 |
| Comparative Example 10 | 6.5 | 4.5 |
| Comparative Example 11 | 9.0 | 3.6 |
| Comparative Example 12 | 12.2 | 8.0 |

Example 17, Comparative Examples 13, 14

The bonding strength and the bonding durability of the bonding composition of Example 9 to the enamel and the dentin of bovine teeth that had been etched with an acid were compared with those to the enamel and the dentin of bovine teeth not having been etched with an acid. For the former, bovine teeth were etched in the manner mentioned below. The data obtained are given in Table 6. (For reference, the data of Example 9 are also given in Table 6.) To etch them, a commercially available, phosphoric acid etchant (Kuraray's K-etchant; aqueous 38% phosphoric acid solution) was applied to the surface of each bovine tooth to which the bonding composition is to be applied, and kept at room temperature for 30 seconds. Next, the processed surface of each bovine tooth was washed with running water for 30 seconds, and then exposed to clean compressed air by which water was blown off and the surface was dried. From the data, it is understood that the bonding strength and the bonding durability of the bonding composition of the invention to the non-etched objects are on the same level as those to the phosphoric acid-etched objects. This supports the excellent bonding ability of the bonding composition of the invention even to non-etched objects.

TABLE 6

|  | Condition for Treatment | Bonding Strength (MPa) | Bonding Durability (MPa) |
| --- | --- | --- | --- |
| Example 9 | Bovine dentin not etched | 18.6 | 17.6 |
| Comp. Ex. 13 | Bovine dentin etched | 18.3 | 17.0 |
| Example 17 | Bovine enamel not etched | 21.2 | 17.7 |
| Comp. Ex. 14 | Bovine enamel etched | 19.0 | 17.8 |

Example 18

According to the method employed hereinabove for preparing tooth samples for measurement of the bonding strength of bonding compositions thereto, a bovine tooth was polished to prepare a tooth sample with the dentin exposed. A part of the polished dentin surface was masked with a varnish (Kuraray's Protect Varnish), and the bonding composition of Example 5 was applied to the sample to broadly cover both the masked and non-masked area, then left as such for 60 seconds, and thereafter exposed to air streams to evaporate the volatile components of the composition. Next, a polymerizable resin (Kuraray's pit and fissure sealant, Teethmate F1) was applied thereover to form a thick film thereon, and exposed to light to cure the resin. The thus-processed bovine tooth sample was cut into two parts that contained both masked part and non-masked part, and polished. The cross section of each part was observed with an electronic microscope (Hitachi's S-510). As a result, a level difference of about 0.5 microns was found between the masked part and the non-masked part. This indicates that the bonding composition dissolved the dentin of the tooth sample.

On the other hand, the bonding composition of Example 5 was applied to the surface of the polished bovine tooth sample with the dentin exposed to form a thick film thereon. After left as such for 1 minute, the crude product of the bonding composition was collected from the sample by the use of a microsyringe and its pH was measured. The pH of the collected product was higher by 0.7 than that of the unused composition. From this, it is understood that the acid ingredient of the bonding composition reacted with the tooth and formed its calcium salt, whereby the product of the composition was neutralized. This supports the self-etching ability of the bonding composition of the invention.

Example 19, Comparative Example 15

Two drops of the bonding composition of Example 1 were put into a test tube, and the solvent (water) was removed by air blowing thereto. This was exposed to light from the same light emitter as that used in Example 1, and immediately it gave heat of polymerization. Thus, it cured extremely rapidly. For comparison, the two-liquid type bonding composition of Example 2 of Japanese Patent Laid-Open No. 45510/1985 was tested in the same manner. Briefly, one drop of liquid D and one drop of liquid B were mixed in a test tube, and the solvent was removed by air blowing thereto. While left at 23° C., the test tube was monitored for the temperature change by feeling it with fingers at regular intervals of 10 seconds. After 30 to 40 seconds, it gave heat, and began to polymerize.

As described in detail hereinabove with reference to its embodiments, the bonding composition of the invention comprises a polymerizable compound having an acid group, a water-soluble film-forming agent, water and a curing agent, in which the calcium salt of the acid is insoluble in water and in the film-forming agent, and the film-forming agent is a polymerizable compound and is miscible with a physiological saline solution. Accordingly, the bonding composition has the function of self-etchability, and, when used in dental treatment, it does not require any pretreatment such as etching with phosphoric acid or priming of teeth. The bonding composition has high bonding strength and good bonding durability. Its bonding strength stably lasts for a long period of time.

In case where a form-retaining agent is added to the bonding composition, the strength of the bonding layer of the composition is much increased, and, in addition, the bonding layer can provide the desired thickness. Accordingly, polymerization inhibition in the bonding interface that may be caused by oxygen in air can be prevented. The bonding interface can be smoothly polymerized and cured to provide increased and stable bonding strength of the cured bonding layer.

In addition, as so mentioned above, the dental with the bonding composition of the invention does not require etching or priming. Therefore, the bonding composition reduces the dentists labor and time for treatment. In addition, the time for which the patients must open their mouth can be shortened, and the patients' pain can be reduced. Thus, the bonding composition of the invention is useful in dental treatment.

While the invention has been described in detail and with reference to specific embodiments thereof, it will be apparent to one skilled in the art that various changes and modifications can be made therein without departing from the spirit and scope thereof.

The priority document of the present application, Japanese Patent Application No.132085/1999, filed May 13, 1999, is incorporated herein in its entirety by reference.

Obviously, numerous modifications and variations on the present invention are possible in light of above teachings. It is therefore to be understood that within the scope of the appended claims, the invention may be practiced otherwise than as specifically described herein.

What is claimed is:

1. A bonding composition for tooth tissue, comprising:
    a mixture of a (meth)acryloyloxyalkyl phosphate,
    a water-soluble film-forming agent,
    a form-retaining agent selected from the group consisting of a sand balloon, a glass balloon, a glass fiber having a mean particle size between 1 and 300 micron, a piece of hollow glass fiber, a glass bead, glass powder, powder of a natural mineral, beads of a cross linked polymer, flakes of a cross linked polymer and an organic/inorganic composite material containing a cross linked polymer,
    water, and
    a curing agent;
    wherein a calcium salt formed from said (meth) acryloyloxyalkyl phosphate is insoluble in water;
    wherein said film-forming agent is a polymerizable compound; and
    wherein said film-forming agent is miscible with a physiological saline solution.

2. The bonding composition according to claim 1, wherein an amount of said (meth)acryloyloxyalkyl phosphate is between 0.1 and 50% by weight per 100% by weight of said bonding composition.

3. The bonding composition according to claim 1, wherein said film-forming agent is selected from the group consisting of a (meth)acrylate, an acrylamide, a crotonate, a cinnamate and mixtures thereof.

4. The bonding composition according to claim 3, said (meth)acrylate has a hydrophilic group selected from the group consisting of a hydroxyl group, a carbonyl group, an amino group, an ammonium salt group, a phosphonium salt group, a sulfonic acid salt group, an ether bond, a cyclic ether group and an acyl group.

5. The bonding composition according to claim 1, wherein said film-forming agent is a polymerizable compound comprising 2-hydroxyethyl methacrylate.

6. The bonding composition according to claim 1, wherein said film-forming agent comprises a hydrophilic monomer, a monofunctional (meth)acrylate and/or a polyfunctional (meth)acrylate.

7. The bonding composition according to claim 1, wherein a blend ratio of said monofunctional (meth)acrylate and/or said polyfunctional (meth)acrylate is 0.1–40 parts by weight of a total weight of said bonding composition.

8. The bonding composition according to claim 1, wherein said curing agent is a polymerization initiator or a mixture of a polymerization initiator and a polymerization promoter.

9. The bonding composition according to claim 8, wherein said polymerization initiator is selected from the group consisting of a photo-polymerization initiator, a thermal polymerization initiator and mixtures thereof.

10. The bonding composition according to claim 8, wherein said polymerization initiator is soluble in water.

11. The bonding composition according to claim 8, wherein said polymerization initiator is selected from the group consisting of an α-diketone, a ketal, an anthraquinone, a thioxanthone, a benzoin alkyl ether, an acylphosphine oxide and mixtures thereof.

12. The bonding composition according to claim 8, wherein said thermal polymerization initiator is selected from the group consisting of a diacyl peroxide, a peroxy ester, a dialkyl peroxide, a peroxy ketal, a ketone peroxide, a hydroperoxide and mixtures thereof.

13. The bonding composition according to claim 8, wherein said polymerization promoter is selected from the group consisting of an amine, a sulfinic acid, a salt of an amine, a salt of a sulfinic acid and mixtures thereof.

14. The bonding composition according to claim 1, wherein an amount of said curing agent is between 0.05 and 20% by weight per 100% by weight of said bonding composition.

15. The bonding composition according to claim 1, wherein said form-retaining agent is a particle.

16. The bonding composition according to claim 15, wherein the mean particle size of said particle is between 1 and 300 micron.

17. The bonding composition according to claim 1, wherein said form-retaining agent is a cross-linked polymer particle.

18. The bonding composition according to claim 1, wherein an amount of said form-retaining agent is between 0.5 and 20% by weight per 100% by weight of said bonding composition.

19. The bonding composition according to claim 1, wherein a pH value of an aqueous 1 weight % solution of said (meth)acryloyloxyalkyl phosphate is between 1.8 and 2.5.

20. The bonding composition according to claim 1, wherein said composition is a liquid.

* * * * *